United States Patent [19]
Toth

[11] 4,288,164
[45] Sep. 8, 1981

[54] METHOD AND APPARATUS FOR VIEWING GLOWING OBJECTS

[75] Inventor: James M. Toth, Lyndhurst, Ohio

[73] Assignee: Republic Steel Corporation, Cleveland, Ohio

[21] Appl. No.: 59,025

[22] Filed: Jul. 19, 1979

[51] Int. Cl.³ .................. G01N 21/55; G01N 21/88; B07C 5/342; G05D 25/00
[52] U.S. Cl. ........................... 356/445; 209/587; 350/268; 350/276 R; 356/237
[58] Field of Search .................. 356/23-26, 356/445-448, 51, 429-431; 315/241 S; 209/587; 350/268, 276 R, 276 SL, 266, 272, 274, 269

[56] References Cited
U.S. PATENT DOCUMENTS

| | | | |
|---|---|---|---|
| 1,203,291 | 10/1916 | White | 109/49.5 |
| 1,374,965 | 4/1921 | Tate | 350/268 |
| 1,408,386 | 2/1922 | Newton | 296/97 F |
| 1,811,481 | 6/1931 | Stone | 356/25 |
| 1,954,962 | 4/1934 | Tate | 350/62 |
| 2,066,680 | 1/1937 | Gieskieng et al. | 350/268 |
| 2,084,681 | 6/1937 | Grun | 219/147 |
| 2,441,887 | 5/1948 | Kopp | 296/97 F |
| 2,514,990 | 7/1950 | Dewan | 219/147 |
| 2,898,801 | 4/1959 | Rockafellow | 350/272 |
| 2,986,063 | 5/1961 | Etzenhouser | 350/268 |
| 3,005,374 | 10/1961 | Thomas | 350/268 |
| 3,303,271 | 2/1967 | Hecker | 358/225 |
| 3,435,213 | 3/1969 | Colbow et al. | 250/458 |
| 3,615,136 | 10/1971 | Kamm | 356/25 |
| 4,118,732 | 10/1978 | Ichijima et al. | 358/101 |

*Primary Examiner*—John K. Corbin
*Assistant Examiner*—Bruce Y. Arnold
*Attorney, Agent, or Firm*—Watts, Hoffmann, Fisher & Heinke Co.

[57] ABSTRACT

A method for viewing a glowing steel body such as a billet for flaw inspection or identification. The process identification includes the step of providing identifying indicia on a surface of the billet. The billet is viewed by illuminating the billet with a source of bright light to create shadows so that the indicia or flaws can be seen, and viewing the billet from behind a protective device which permits intermittent viewing of the object. Apparatus for carrying out the method includes a shutter by which the light emitted by the billet is attenuated. The shutter employs a pair of rotatable disks having spaced, parallel axes of rotation and the disks are overlapped near their peripheries. Each disk includes a viewing opening disposed near its periphery. When the disks are rotated in the same direction and at different angular speeds, the viewing openings periodically are aligned for short periods of time. The apparatus also includes a pulsed light source having a xenon flash lamp connected across capacitors. The shutter includes a timing mechanism so that the lamp is flashed when the shutter permits viewing of the object.

23 Claims, 6 Drawing Figures

METHOD AND APPARATUS FOR VIEWING GLOWING OBJECTS

BACKGROUND OF THE INVENTION

1. Field of the Invention

The invention relates to identifying glowing objects during a manufacturing operation and, more particularly, to a method and apparatus wherein a brightly glowing steel object may be identified.

2. Description of the Prior Art

In a steel manufacturing operation where objects such as billets are being processed, the billets typically are manufactured in one facility; cooled; and shipped to another facility where they may be worked into products. For example, billets may be made in one manufacturing facility and shipped to a rolling mill where they are reheated to temperatures on the order of 2200-2400 degrees Fahrenheit. After the billets have been reheated, they are worked to form products such as sheet steel.

Steel is manufactured in batches known as heats. Since a wide variety of alloys are manufactured, and since an individual heat will make in excess of 200 tons of a given alloy, it has become uncommon to have any two successive heats of the same alloy. Rather, it has become commonplace to make a heat to fill a given order for a specific alloy.

Since the billets of one heat often differ chemically from the next, it is obviously important to be able to avoid mixing the billets of one heat with those of another, but a problem exists in that billets can shift position in a reheat furnace. Accordingly, simply counting the billets as they enter and leave the reheat furnace does not necessarily identify billets exiting the furnace. Further it is obviously possible to simply miscount the number of billets.

Various expedients have been tried to assist in identification of reheated billets. Bricks have been placed on selected billets but they sometimes fall off or a brick may shift to another billet. Studs have been welded to, and wires wrapped around, billets. These tend to get rubbed or broken off the billets as the billets are transported through a furnace.

Since billets may be heated as high as 2400° in the reheat furnace, it should be apparent that most conventional product marking techniques simply cannot be used. Whatever markings may have been tried in the past, such as the described bricks, studs and wire, are at best difficult to see because they can only be viewed from a distance and are hard to see because a hot billet glows brightly.

Because of the described and other problems inherent in billet identification, most steel manufacturing facilities have resorted to simply counting the billets and standing the consequences which result when on occasion billets get miscounted or mixed.

Another problem in steel manufacture is, it is not uncommon for slabs to have or to develop surface defects. With a heated slab there has been no successful and practical technique for determining what surface defects exist. Accordingly the normal procedure is to allow a slab to cool, inspect for and remove surface defects and then reheat the slab for further processing.

SUMMARY OF THE INVENTION

The present invention provides a new and improved technique for viewing glowing objects for identification of the object and/or of surface defects. The technique overcomes the described and other problems of prior procedures. When used for identification the invention includes the step of marking the surface of the objcts with indelible identifying indicia. The marking may be accomplished in a variety of ways such as by painting with refractory cement or removing portions with a torch, or by drilling. It has been discovered that the indicia can be observed by eye and the steps required to achieve this observation form a part of the present invention.

The indicia may be observed by illuminating the object with a source of bright light sufficient to "overpower" the light emitted by the object and to reveal reflectivity differences and create shadows on the surface of the object. The method also contemplates viewing the object from behind a protective device which permits intermittent visualization of the object and, accordingly, protection for the eyes of the observer. Although an object may be very hot and appear brightly glowing to the naked eye, when the object is viewed through the apparatus of this invention the object will appear as if it were at room temperature. This occurs because the hot object is seen primarily by light reflected by the object rather than by light emitted from it. The preferred viewing device is a novel stroboscope, using as a light source a flash lamp pulsed in synchronism with a novel shutter.

The light emitted by a hot billet and the light required to reveal reflectivity differences on the surface of the objects impose greater demands than those imposed on prior devices employed for similar purposes. Accordingly the invention encompasses concepts embodied in a shutter capable of attenuating light from the glowing objects more effectively than prior shutters.

The shutter includes a pair of disks supported for rotation in generally parallel planes, the centers of rotation of the disks being spaced. Each disk includes a transparent or viewing portion disposed near the periphery of the disk. The disks are overlapped near their peripheries so that the viewing portions periodically are aligned upon rotation of the disks.

The disks are rotated in the same direction, but at different speeds. Accordingly, the viewing portions are aligned only once for a given plurality of disk rotations, and even then for only a very small period of time because the viewing portions are moving oppositely with respect to each other. By appropriate configuration of the viewing portions and by precisely controlling rotational speed of the disks, the duration and frequency of shutter openings can be selected independently of each other.

It has been found that a xenon flash lamp discharged across capacitors provides a sufficiently brilliant light. Commercially available xenon flash lamps provide a light on the order of 500,000 lumens for approximately 10 microseconds, and require a capacitor charge time of approximately 80 milliseconds. The shutter according to the invention is maintained open for adjustable time periods typically of the order of approximately 50 microseconds. The opening is repeated at adjustable frequencies typically approximately every 80 milliseconds, roughly the charge time of the capacitors. This operation blocks emitted light from the glowing billet most of the time allowing only about 1/1400 of the billet emitted light through the shutter to the eye of the viewer.

A coincidence detection circuit is provided to synchronize the pulsing of the xenon lamp with alignment of the viewing portions of the disks. Each disk has a timing notch disposed at or near its periphery and spaced a predetermined radial distance from the viewing portion. Photocells, one for each disk, are connected to the coincidence circuit and disposed near the periphery of each disk and are spaced the predetermined radial distance from the aligned viewing portions. By this construction both photocells may be activated by the simultaneous appearance of the timing notches at the photocells and an electrical signal may be generated by the coincidence circuit. The electrical signal is used to trigger the xenon lamp.

Each disk is driven by a drive pulley and the pulleys are connected by a timing belt. The pulleys are of different diameters (11/12 ratio) so that the disks rotate at different speeds and the viewing portions are aligned only after a certain number of disk rotations have occurred. It has been found that if the larger pulley is rotated at 7920 revolutions per minute, then the smaller pulley will rotate at 8640 revolutions per minute and 12 evenly spaced viewing portion alignments per second will be produced. The desirable characteristics of a 1400 to 1 filtration factor, shutter open time of approximately 50 microseconds, and repetition rate of approximately one repetition each 80 milliseconds thus are obtained.

Single disk shutters, which are well known to those skilled in the art, do not provide the high filter factor (shutter repetition rate divided by shutter open time per cycle) that the dual disk shutter of this invention provides. A single disk shutter of the same dimensions as the dual disk system described can provide a filter factor of only 64 to 1. The dual disk system described, by virtue of its nearly double shutter speed and 1/12 repitition rate for a given disk rpm, provides a filter factor 22 times greater (1400 to 1).

One of the novel aspects of the present invention is that while the novel viewing apparatus has been, and will be, described as, and is capable of being used as, a stroboscope, it in fact is not so used. That is, it is not used in the sense that the stroboscope is a device which provides seemingly motionless viewing of a rapidly moving object. Rather, the apparatus of this invention is used to permit viewing of a very hot and glowing billet or slab which in fact might be stationary or nearly so at the time of viewing.

According to another aspect of the present invention, surface defects in hot slabs or other objects can be seen and detected without cooling the slab. Thus, the slab can be inspected and if it is defect free, further processed without cooling and reheating. If defects are seen, their locations may be marked by, as an example, a process and apparatus such as that disclosed and claimed in U.S. Pat. No. 4,127,815, issued to Vild et al on Nov. 28, 1978, under the title "Method and Apparatus for Marking an Article Following Flaw Detection Using a Fusible Metal Powder". Flaws can then be removed by known techniques such as scarfing and then the slab will be further processed without the delay and expense of cooling and reheating the slab.

Whether used for identification or flaw inspection, this invention provides a method of determining surface characteristics of a hot, glowing metallic body. In each case a high speed shutter assembly is positioned along a path of light transmission from the glowing body to a viewing station. The shutter is operated to allow intermittent cyclic light transmission from the body to the station and the transmitted light is used to determine physical characteristics of the body. Further processing uses procedures established in accordance with the determined characterics to produce a finished product.

Additional features of the invention will become apparent from the following detailed description of a preferred embodiment of the invention made with reference to the accompanying drawings which form a part of the specification.

DESCRIPTION OF THE PREFERRED EMBODIMENT

Figure 1:
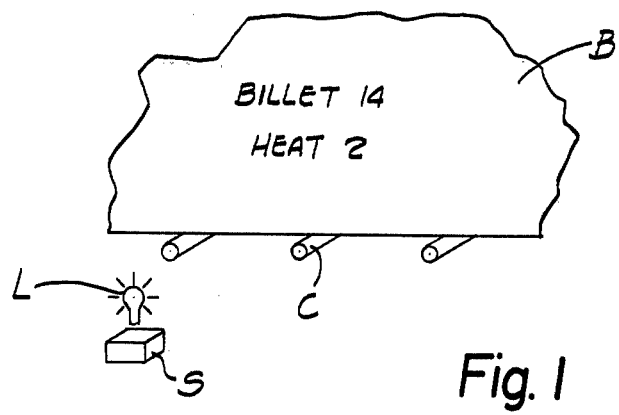
FIG. 1 is a schematic view of billet identification in accordance with this invention.
Figure 6:
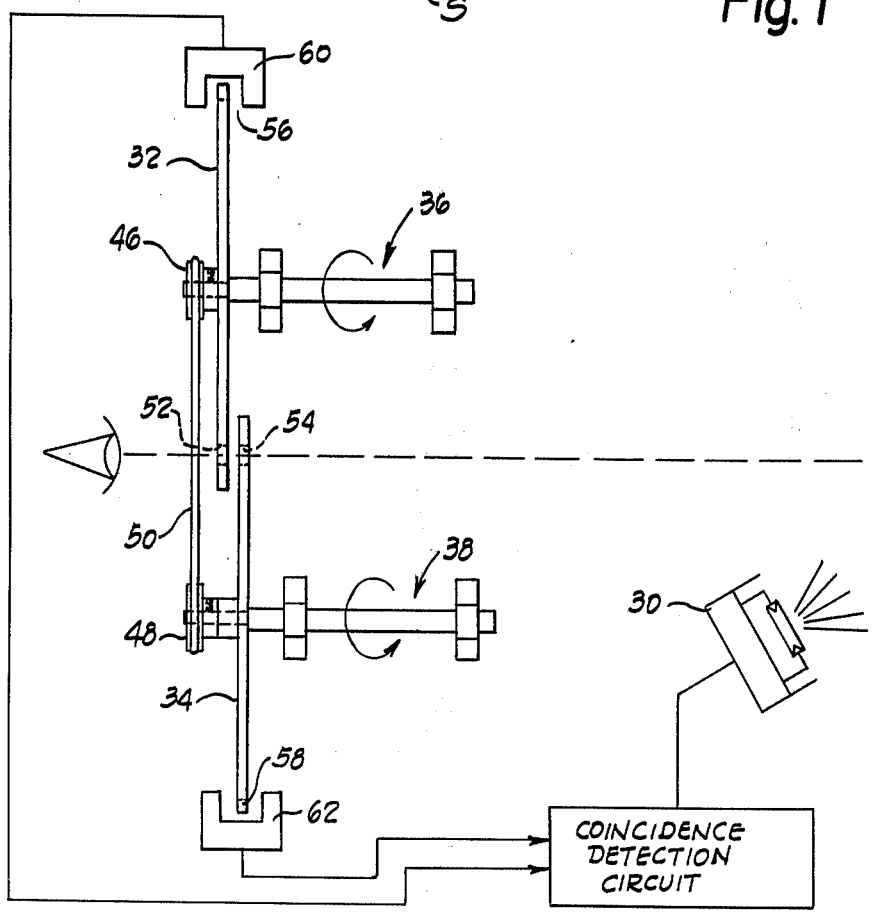
FIG. 6 is a schematic representation of the shutter circuit compounents and the stroboscope in use.

FIG. 1 is a schematic showing of a steel billet and a viewing mechanism for use in accordance with this invention. In FIG. 1, a fragmentary portion of a billet is shown schematically at B supported on a schematically shown conveyor C. As shown, the billet B has indicia inscribed in its surface for identification. The pictured inscription is billet No. 14, heat No. 2 to suggest that this schematically represents the fourteenth billet of the second heat from a given steel making vessel. A light source L is positioned to illuminate the billet in synchronism with a stroboscopic viewer S. Bright flashes from light source L permit an observer to read the indicia inscribed on the billet.

Figure 2:
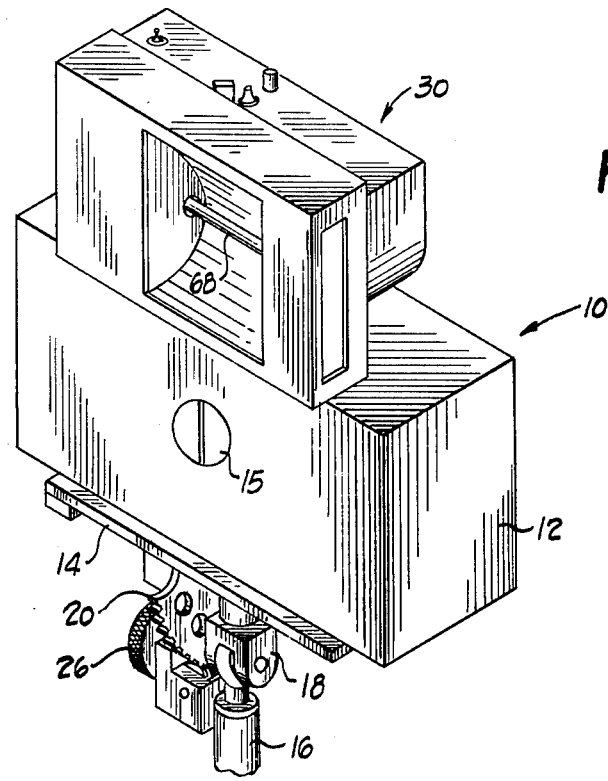
FIG. 2 is a perspective view of a stroboscope according to the invention.

In practice, the light source L and the stroboscopic viewer are combined as a single stroboscopic unit shown in perspective view at 10 in FIG. 2. The stroboscope includes a housing 12 connected to a support plate 14. A light admitting opening 15 is provided in the face of the housing.

The stroboscope is mounted on a rotatable mast 16 by a support bracket 18. The support bracket is fixed to the support plate 14. A sector gear 20 is interposed between the support plate 14 and the mast 16 to enable the stroboscope to be inclined for alignment with a work piece to be observed. The sector gear is controlled by a worm gear 21 and a thumb wheel 22 (FIGS. 3 and 4) carried by a bracket 24. The bracket is attached directly to the mast 16. A set screw 26 is threaded through the side of the bracket 24 and selectively to engage the side of the sector gear 20. This construction assures that the stroboscope will be locked in an adjusted position which cannot be disturbed accidentally.

Figure 3:
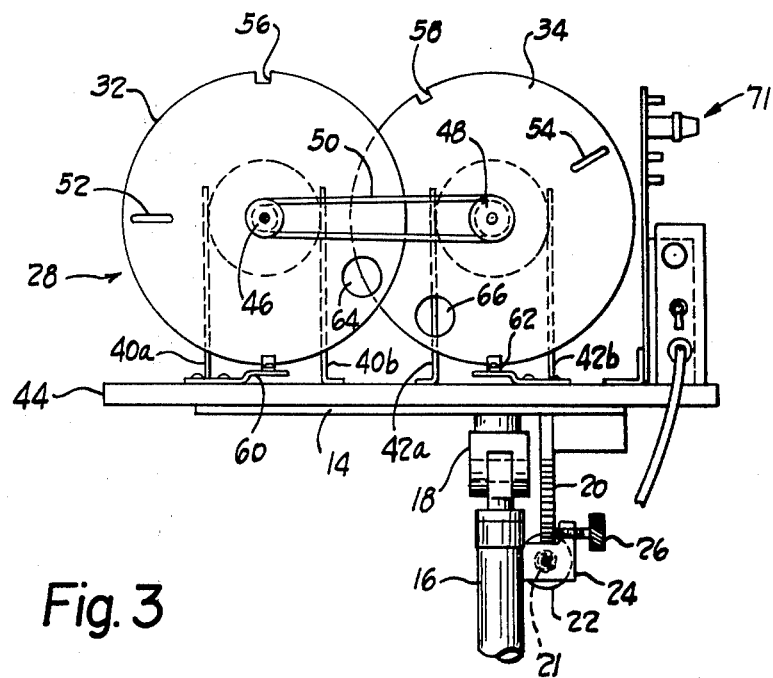
FIG. 3 is a front elevational view, on an enlarged scale when compared with FIG. 2, of a shutter according to the invention and with protective covers removed.
Figure 4:
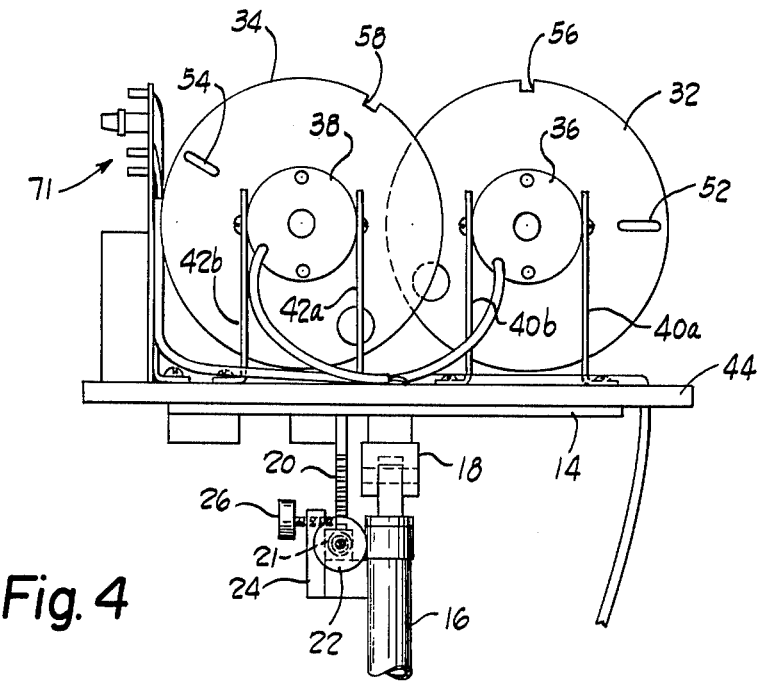
FIG. 4 is a real elevational view of the shutter of FIG. 3.

A shutter assembly 28, FIGS. 3 and 4, is mounted on the support plate 14. Normally the shutter assembly is disposed inside the housing while a light source 30 is supported at the top of the housing.

The shutter assembly includes a pair of rotatable disks 32, 34 supported for rotation in closely spaced parallel planes. The disks are supported for rotation by electric motors 36, 38, respectively. In use, one of the motors is powered while the other serves simply as a bearing support for the disk carried by it as well as an alternate source of power. The axes of rotation of the motors and discs are parallel to one another and to a viewers line of sight.

The motors 36, 38 are carried by support brackets 40a, 40b and 42a, 42b respectively. In turn, the brackets are carried by a base 44 which is fastened to the support plate 14. The base 44 also serves to support the housing 12.

The motors 36, 38 are AC-DC universal motors rated to 1/10 horsepower at 8,000 revolutions per minute. The disks are keyed to the drive shafts of the motors along with pulleys 46, 48, FIG. 3. A timing belt 50 is reeved about the pulleys 46, 48 to interconnect the pulleys and guarantee synchronism of the disks. The pulleys have different diameters so that one disk will rotate at a different speed than the other. Here, the ratio of pulley diameters has been selected at 11/12; accordingly, one disk will rotate 12 times for every 11 rotations of the other disk.

The disk 32 includes an elongate viewing slot or portion, 52 near the periphery of the disk. The dimension of the viewing slot 32 is disposed radially of the disk. The second disk 34 includes an identically configured viewing slot or portion 54.

As shown in FIGS. 3 and 4, the axes of rotation of the two disks are spaced so that the disks overlap slightly so that the two viewing slots can be aligned. When the slots are aligned they permit light to pass through the light admitting opening 15 and the disks to an observer. Assuming that both disks rotate in the same direction the viewing slots 52, 54 will be moving in opposite directions shortly before, during and after alignment. Accordingly, the relative speed between the slots will be greatest whenever they are aligned.

The first disk 32 includes a timing slot, or notch 56 formed near the periphery of the disk and circumferentially spaced from the viewing slot 52 a predetermined distance. The second disk 34 includes a similar notch 58 circumferentially spaced the same distance from its corresponding viewing slot 54. Photocell assemblies 60, 62 are fixed to the base 44. The photocells 60, 62 are positioned such that peripheral portions of the disks 32, 34 prevent light transmission from source to detector except when the notches 56, 58 pass. Each of the viewing slots is spaced radially inwardly from the periphery of its disk so that only the timing notches effect operation of the photocells.

The disks 32, 34 include relieved portions 64, 66 respectively. Each relieved portion is spaced generally diametrically from the slot and notch of its disk. The relieved portions serve to balance the disks by compensating for material removed from the disk to form the viewing slots and timing notches.

The light source 30 includes a high intensity flash lamp 68. An acceptable lamp assembly is manufactured by the General Radio Corporation, Model Strobolume Type 1540, and includes a xenon flash lamp connected across capacitors. This lamp will provide a pulsed light source of approximately 50 million beam candle power, having a capacitor discharge time of approximately 10 microseconds, and having a maximum repetition rate at maximum flash intensity of about 13 flashes per second (about 80 milliseconds between flashes).

Figure 5:
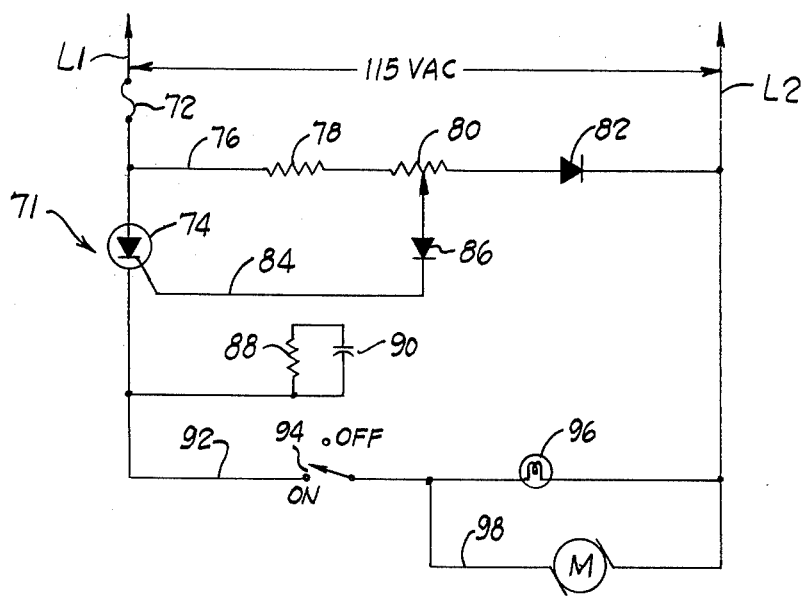
FIG. 5 is a schematic wiring diagram of a motor speed control used with the invention.

A motor speed control 71 is mounted on the base 44 and within the housing 12. The motor speed control permits selective control of the speed of the motors and, hence, the disks. Referring now to FIG. 5, a pair of leads L1, L2 are connected to an AC source of electrical power. A fuse 72 and a silicon controlled rectifier (SCR) 74 are in series with lead L1. An acceptable SCR is manufactured by the General Electric Company, Model SC40B.

A line 76 is across the leads L1, L2 and includes, in series, a resistor 78, a potentiometer 80, and a diode 82. The diode 82 is a blocking diode permitting current flow in the line 84 during one half the AC cycle while blocking current flow during the other one half cycle. A line 84, including a rectifying diode 86, connects the potentiometer to the SCR to convey half wave D.C. trigger signals. The resistor 78 has a rating of one watt at 5600 ohms and the potentiometer 80 has a rating of two watts at 1000 ohms. The diodes 82, 86 are identical Model IN50G1 diodes manufactured by the General Electric Company.

An RC circuit is connected to the SCR 74 to provide a delay between the arrival of the SCR input signal and the trigger signal. The RC circuit comprises, in parallel, a resistor 88 and a capacitor 90. The resistor has a rating of one-half watt at 1000 ohms and the capacitor is rated at two microfarads.

A line 92 connects the lead lines L1, L2 and includes a motor control switch 94 and a pilot light 96 in series with each other. A line 98 connects either the motor 36 or the motor 38 in parallel with the light 96. When the switch 94 is closed, current flows to the motor, and the pilot light is energized to indicate that the motor is under power.

The foregoing arrangement of components provides a half-wave phase control for the motor. The diode 86 rectifies the line current and the potentiometer provides a variable control of that portion of the current which actually is sent to the motor. By appropriate adjustment of the potentiometer 80, the output of the motor speed control can be adjusted as desired and the speed of the motor can be controlled precisely to provide the desired viewing characteristics.

In use, the stroboscope, functioning as a viewer, is adjusted until it is directed at the portion of a billet to be viewed. This adjustment is accomplished by rotating the unit 10 about the axis of the mast 16 and adjusting the thumb wheel 22 to provide the desired angle of elevation. Either the motor 36 or the motor 38 is then energized to cause the disks 32, 34 to rotate. Whenever the viewing slots 52, 54 come into registry, the photocell assemblies emit concurrent signals. These concurrent signals cause the coincidence circuit to fire the flash lamp 68 in synchronism with the slot alignment.

The combination of the filtration effect of the rotating disks which substantially eliminates much of the emitted light of the billet from view and the intensity of the repeatedly flashed high powered flash tube creates shadow conditions such that the operator can read, in the example shown in FIG. 1, the designation billet 14, heat 2.

The speed of the energized motor can be adjusted by adjusting the variable potentiometer 80. The speed adjustments are for reasons different than nomal speed adjustments of a stroboscope. That is, in a typical stroboscope use, adjustment of the repetition rate of the light flash is typically for the purpose of bringing it into synchronism with a moving object such as a rotating wheel to permit viewing similar to that which is possible when the wheel is stationary. Here the speed adjustment is used for the entirely different purpose of increasing, or decreasing, the filtration effect of emitted light and providing the desired shadow contrast so that a provided indicia, or a flaw being examined, can be seen, and to keep the repetition rate within the limitations imposed by the strobe light design.

The novel use of the novel stroboscope as a viewer thus provides an effective, reliable technique by which glowing objects such as billets emerging from a reheat furnace can be viwed for inspection and/or identification. The shutter permits far greater attenuation of light than heretofore possible because of its excellent control of the length of viewing slot alignments (extremely short shutter open time) and the repetition rate of viewing slot alignments (relatively long repetition period). The strobe light produces a sufficiently brilliant flash of light that identifying indicia or significant defect on or in the surface of a billet can be recognized with ease.

While a specific embodiment of the invention has been described, it will be obvious to those skilled in the art that changes and modifications may be made without departing from the invention. It therefore is intended in the appended claims to cover all such changes and modifications that fall within the true spirit and scope of the invention.

What is claimed is:

1. A method of determining surface characteristics of a quantity of steel during an intermediate stage in the manufacture of a finished steel product wherein the quantity of steel is in a hot, glowing, solid state comprising:
   (a) illuminating the quantity of glowing steel with a source of bright light to create differentiating shadows so that surface indentations may be viewed and identified;
   (b) determining surface characteristics of the quantity of steel by viewing the hot and glowing steel from behind a protective device which permits intermittent visualization of the glowing steel; and
   (c) further processing the steel in accordance with information derived by such determination.

2. A method of identifying a hot object in a metal manufacturing operation comprising:
   (a) providing a discernable identifying indicia on a surface of the object which indicia are capable of producing shadows;
   (b) illuminating the object with a source of bright light when the object is hot and glowing to establish discernable shadows so the provided indicia can be viewed; and,
   (c) identifying the object by viewing the indicia.

3. A method of identifying a quantity of steel during an intermediate stage in the manufacture of a finished steel product wherein the quantity of steel is in a hot, glowing, solid state comprising:
   (a) providing identifying indicia on a surface of the quantity of steel which indicia are capable of producing shadows;
   (b) illuminating the glowing steel with a source of bright light to create differentiating shadows so that the identifying indicia may be viewed and the quantity of steel identified; and,
   (c) viewing the hot and glowing steel from behind a protective device which permits intermittant visualization of the glowing steel and thereby identifying the steel.

4. The method of claim 3, wherein the step of viewing the steel occurs in conjunction the step of illuminating the steel.

5. A method for viewing a glowing object, comprising the steps of:
   (a) providing a light source of sufficient intensity to reveal reflectivity differences on the surface of the object;
   (b) pulsing the light source at a predetermined frequency;
   (c) attenuating substantially all of the light emanating from the object at those times when the light source is not activated; and,
   (d) transmitting light emanating from the object and the light source at times when the light source is activated.

6. A method for viewing a glowing object, comprising the steps of:
   (a) blocking light emanating from the object for a predetermined period of time;
   (b) transmitting light emanating from the object for a period of time equal to a fraction of the period of time the light is blocked;
   (c) illuminating the object with a light source of sufficient intensity to reveal reflectivity differences on the surface of the object, the step of illuminating occurring intermittently;
   (d) adjusting the duration of illumination by the light source to a period of time approximating that of the step of transmitting; and,
   (e) coordinating the steps of transmitting and illuminating so that they occur substantially simultaneously.

7. A method for viewing a glowing object, comprising the steps of:
   (a) illuminating the object periodically with a pulsed light source of sufficient intensity to reveal reflectivity differences on the surface of the object;
   (b) blocking light emanating from the object for a period of time;
   (c) transmitting light emanating from the object periodically;
   (d) adjusting the frequency and duration of light transmissions to values making the indicia on the surface of the object discernible; and,
   (e) coordinating the steps of illuminating and transmitting so that the object is viewable when the light source is pulsed.

8. A method of observing identifying indicia on the surface of a hot steel billet, comprising:
   (a) illuminating the billet periodically with a pulsed light of sufficient intensity to reveal reflectivity differences on the surface of the billet;
   (b) blocking light emanating from the billet for a substantial period of time;
   (c) transmitting light emanating from the billet periodically;
   (d) adjusting the frequency and duration of light transmissions to minimum values where indicia on the surface of the billet are discernible; and,
   (e) coordinating the steps of illuminating and transmitting so that the billet is viewable only when the light source is pulsed.

9. A mechanism to permit a viewing of a glowing steel billet or the like, comprising:
   (a) a pair of relatively movable members each having portions defining a relatively small viewing opening;
   (b) supporting and drive structure drivingly connected to the members and adapted to drive the members along repetitive paths of motion which periodically bring the openings into object-viewing alignment;

(c) the paths of motion being such that the portions defining the openings are traversing path portions that are directionally different when the openings are aligned;

(d) the members being of sufficient mass and opacity to protect the vision of an operator viewing a brightly glowing object and block the operation's view of the object except when the openings are aligned;

(e) a source of light for illuminating an object being viewed; and, (f) a source of light-energizing power for energizing the light source at least on occasions when the openings are aligned.

10. The mechanism of claim 9, wherein the path portions are opposed.

11. The mechanism of claim 9, wherein the light source is pulsed in synchronism with opening alignment.

12. A mechanism for viewing a glowing object such as a heated billet, comprising:

(a) a first member having an open portion through which an object may be viewed, the first member being supported for rotation about an axis;

(b) a second member having an open portion through which such object may be viewed, the second member being supported for rotation about an axis displaced from the axis of rotation of the first member, the open portion of the second member alignable periodically with the open portion of the first member to permit intermittent viewing of such object;

(c) a pulsed light source to illuminate such object periodically; and, (d) circuitry to pulse the light when the open portions are in alignment.

13. The mechanism of claim 12, wherein a member drive means is connected to the members to rotate the first member at a speed greater than it rotates the second member so that the open portions are aligned only once for a given plurality of first member rotations.

14. The mechanism of claim 12, wherein the members are rotatable in the same direction so that the open portions move oppositely with respect to each other during alignment.

15. The mechanism of claim 12, wherein:

(a) the first member includes a timing portion spaced a predetermined distance from the open portion;

(b) the second member includes a timing portion spaced a predetermined distance from the open portion; and, (c) a sensor is provided to determine the relative position of the timing portions so that alignment or misalignment of the open portions can be determined.

16. The mechanism of claim 15, wherein:

the timing portions comprise notches formed in the periphery of the members and, the sensor comprises a photocell, one for each member, the operation of the photocells being affected by the notches but not by the open portions.

17. The mechanism of claim 12, wherein the circuitry includes means responsive to a sensor to generate an electrical signal upon alignment of the open portions, the signal serving as a trigger to initiate pulsing of the light source.

18. The mechanism of claim 12, wherein the members are disks.

19. The mechanism of claim 12, wherein the open portions comprise slots spaced radially inwardly from the periphery of the members.

20. A mechanism for viewing a glowing object such as a heated billet, comprising:

(a) a first member having an open portion through which an object may be viewed, the first member being supported for rotation about an axis;

(b) a second member having an open portion through which such object may be viewed, the second member being supported for rotation about an axis displaced from the axis of rotation of the first member, the open portion of the second member alignable periodically with the open portion of the first member to permit intermittent viewing of such object;

(c) a pulsed light source to illuminate such object periodically;

(d) circuitry to pulse the light when the open portions are in alignment; and, (e) drive means for rotating the members in the same direction and at different speeds.

21. A mechanism for viewing a glowing object such as a heated billet, comprising:

(a) a first member having a viewing opening through which an object may be viewed, the first member being supported for rotation about an axis;

(b) a second member having a viewing opening through which such object may be viewed, the second member being supported for rotation about an axis displaced from the axis of rotation of the first member, the viewing openings being alignable periodically to permit intermittent viewing of such object;

(c) a pulsed light source to illuminate such object periodically;

(d) circuitry to pulse the light when the viewing openings are in alignment;

(e) each of the members including a timing opening;

(f) the viewing openings of each member being spaced radially from the axis of its member by an amount different than the timing opening of its member; and, (g) a pair of photocell assemblies each positioned to be caused to emit signals in response to an associated one of the timing openings but spaced from the viewing openings.

22. A method of inspecting a quantity of steel during an intermediate stage in the manufacture of a finished steel product wherein the quantity of steel is in a hot, glowing, solid state comprising:

(a) illuminating the glowing steel with a source of bright light to establish differentiating shadows when surface flaws are present so that the flaws may be viewed and their locations established;

(b) viewing the steel while hot and glowing from behind a protective device which permits intermittent visualization of the glowing steel;

(c) determining whether shadows are established which represent surface flaws in the steel; and, (d) further processing the steel according to the shadow determination.

23. A method of determining surface characteristics of a hot, glowing metallic body comprising:

(a) positioning a high speed shutter assembly along a path of light transmission from the glowing body to a viewing station;
(b) illuminating the glowing steel with a source of bright light to establish differentiating shadows when such surface characteristics are present so that the characteristics may be viewed and their locations established;
(c) operating the shutter to allow intermittent cyclic light transmission from the body to the station;
(d) using the transmitted light to determine physical characteristics of the body; and,
(e) further processing the body with procedures established in accordance with the determined characteristics to produce a finished product.

* * * * *